US009486292B2

(12) United States Patent
Nelson et al.

(10) Patent No.: US 9,486,292 B2
(45) Date of Patent: Nov. 8, 2016

(54) SYSTEMS AND METHODS FOR REAL-TIME WINDING ANALYSIS FOR KNOT DETECTION

(75) Inventors: Donald Douglas Nelson, Montgomery Village, MD (US); Milan Ikits, Gaithersburg, MD (US); Chih-Hao Ho, Reston, VA (US); Kevin Kunkler, Frederick, MD (US)

(73) Assignee: Immersion Corporation, San Jose, CA (US)

( * ) Notice: Subject to any disclaimer, the term of this patent is extended or adjusted under 35 U.S.C. 154(b) by 2607 days.

(21) Appl. No.: 12/031,642

(22) Filed: Feb. 14, 2008

(65) Prior Publication Data
US 2009/0209978 A1 Aug. 20, 2009

(51) Int. Cl.
*A61B 18/00* (2006.01)
*G09B 23/28* (2006.01)
*D04G 5/00* (2006.01)
*G09B 19/00* (2006.01)

(52) U.S. Cl.
CPC .............. *A61B 34/25* (2016.02); *A61B 34/00* (2016.02); *A61B 34/10* (2016.02); *D04G 5/00* (2013.01); *G09B 19/0076* (2013.01); *G09B 23/28* (2013.01); *A61B 2018/00297* (2013.01)

(58) Field of Classification Search
CPC .............................. G09B 23/28; G09B 23/285
USPC .................................................. 434/262, 267
See application file for complete search history.

(56) References Cited

U.S. PATENT DOCUMENTS 2,524,782 A 10/1950 Ferrar et al.
3,490,059 A 1/1970 Paulsen et al.
3,623,046 A 11/1971 Scourtes
(Continued)

FOREIGN PATENT DOCUMENTS

EP 0 085 518 B1 8/1989
EP 0 470 257 A1 2/1992
(Continued)

OTHER PUBLICATIONS

Adelstein, B., A Virtual Environment System for the Study of Human Arm Tremor, Submitted to the Dept. of Mechanical Engineering in partial fulfillment of the requirements for the degree of Doctor of Philosophy at the Massachusetts Institute of Technology, Jun. 1989, pp. 1-253.
(Continued)

*Primary Examiner* — Nikoali A Gishnock
(74) *Attorney, Agent, or Firm* — Kilpatrick Townsend & Stockton LLP

(57) ABSTRACT

Embodiments of systems, methods, and computer-readable media for real-time winding analysis for knot detection are disclosed. For example, one embodiment of the present invention includes a method having the steps of receiving a first wrapping signal indicating a first wrapping of the simulated thread around a second tool to create a first loop. The method further includes determining a first wrapping direction based at least in part on the first wrapping signal; receiving a first tightening signal indicating a pulling of a first end of the simulated thread through the first loop; determining a first half-hitch based at least in part on the first winding direction and the first tightening signal; and outputting the first half-hitch. In another embodiment, a computer-readable media includes code for a carrying out such a method.

18 Claims, 6 Drawing Sheets

(56) References Cited

U.S. PATENT DOCUMENTS

| | | | |
|---|---|---|---|
| 3,775,865 | A * | 12/1973 | Rowan ........................ 434/262 |
| 3,875,488 | A | 4/1975 | Crocker et al. |
| 4,050,265 | A | 9/1977 | Drennen et al. |
| 4,103,155 | A | 7/1978 | Clark |
| 4,125,800 | A | 11/1978 | Jones |
| 4,148,014 | A | 4/1979 | Burson |
| 4,311,980 | A | 1/1982 | Prusenziati |
| 4,321,047 | A * | 3/1982 | Landis ........................ 434/262 |
| 4,385,836 | A | 5/1983 | Schmitt |
| 4,391,282 | A | 7/1983 | Ando et al. |
| 4,400,790 | A | 8/1983 | Chambers et al. |
| 4,443,952 | A | 4/1984 | Schulien et al. |
| 4,546,347 | A | 10/1985 | Kirsch |
| 4,637,264 | A | 1/1987 | Takahashi et al. |
| 4,639,884 | A | 1/1987 | Sagues |
| 4,678,908 | A | 7/1987 | LaPlante |
| 4,680,466 | A | 7/1987 | Kuwahara et al. |
| 4,692,726 | A | 9/1987 | Green et al. |
| 4,695,266 | A | 9/1987 | Hui |
| 4,699,043 | A | 10/1987 | Violante De Dionigi |
| 4,712,101 | A | 12/1987 | Culver |
| 4,724,715 | A | 2/1988 | Culver |
| 4,728,954 | A | 3/1988 | Phelan et al. |
| 4,734,685 | A | 3/1988 | Watanabe |
| 4,776,701 | A | 10/1988 | Pettigrew |
| 4,789,340 | A * | 12/1988 | Zikria ........................ 434/272 |
| 4,794,384 | A | 12/1988 | Jackson |
| 4,795,901 | A | 1/1989 | Kitazawa |
| 4,799,055 | A | 1/1989 | Nestler et al. |
| 4,803,413 | A | 2/1989 | Kendig et al. |
| 4,811,608 | A | 3/1989 | Hilton |
| 4,815,006 | A | 3/1989 | Andersson et al. |
| 4,819,195 | A | 4/1989 | Bell et al. |
| 4,823,106 | A | 4/1989 | Lovell |
| 4,825,157 | A | 4/1989 | Mikan |
| 4,840,634 | A | 6/1989 | Muller et al. |
| 4,851,771 | A | 7/1989 | Ikeda et al. |
| 4,860,051 | A | 8/1989 | Taniguchi et al. |
| 4,891,889 | A | 1/1990 | Tomelleri |
| 4,906,843 | A | 3/1990 | Jones et al. |
| 4,914,976 | A | 4/1990 | Wyllie |
| 4,935,725 | A | 6/1990 | Turnau |
| 4,935,728 | A | 6/1990 | Kley |
| 4,937,685 | A | 6/1990 | Barker et al. |
| 4,940,234 | A | 7/1990 | Ishida et al. |
| 4,962,448 | A | 10/1990 | DeMaio et al. |
| 4,964,837 | A | 10/1990 | Collier |
| 4,965,446 | A | 10/1990 | Vyse |
| 4,967,126 | A * | 10/1990 | Gretz ................... B25J 9/1612 318/567 |
| 4,982,504 | A | 1/1991 | Soderberg et al. |
| 5,006,703 | A | 4/1991 | Shikunami et al. |
| 5,024,626 | A | 6/1991 | Robbins et al. |
| 5,053,975 | A | 10/1991 | Tsuchihashi et al. |
| 5,062,830 | A | 11/1991 | Dunlap |
| 5,065,145 | A | 11/1991 | Purcell |
| 5,068,529 | A | 11/1991 | Ohno et al. |
| 5,079,845 | A | 1/1992 | Childers |
| 5,086,197 | A | 2/1992 | Liou |
| 5,095,303 | A | 3/1992 | Clark et al. |
| 5,107,080 | A | 4/1992 | Rosen |
| 5,113,179 | A | 5/1992 | Scott-Jackson et al. |
| 5,116,051 | A | 5/1992 | Moncrief et al. |
| 5,125,261 | A | 6/1992 | Powley |
| 5,132,927 | A | 7/1992 | Lenoski et al. |
| 5,138,154 | A | 8/1992 | Hotelling |
| 5,139,261 | A | 8/1992 | Openiano |
| 5,143,006 | A | 9/1992 | Jimenez |
| 5,148,377 | A | 9/1992 | McDonald |
| 5,155,423 | A | 10/1992 | Karlen et al. |
| 5,168,268 | A | 12/1992 | Levy |
| 5,182,557 | A | 1/1993 | Lang |
| 5,195,179 | A | 3/1993 | Tokunaga |
| 5,195,920 | A | 3/1993 | Collier |
| 5,202,961 | A | 4/1993 | Mills et al. |
| 5,204,600 | A | 4/1993 | Kahkoska |
| 5,209,131 | A | 5/1993 | Baxter |
| 5,216,337 | A | 6/1993 | Orton et al. |
| 5,223,658 | A | 6/1993 | Suzuki |
| 5,229,836 | A | 7/1993 | Nagano |
| 5,230,623 | A | 7/1993 | Guthrie et al. |
| 5,235,868 | A | 8/1993 | Culver |
| 5,239,249 | A | 8/1993 | Ono |
| 5,246,316 | A | 9/1993 | Smith |
| 5,247,648 | A | 9/1993 | Watkins et al. |
| 5,254,919 | A | 10/1993 | Bridges et al. |
| 5,275,565 | A | 1/1994 | Moncrief |
| 5,280,276 | A | 1/1994 | Kwok |
| 5,284,330 | A | 2/1994 | Carlson et al. |
| 5,289,273 | A | 2/1994 | Lang |
| 5,296,846 | A | 3/1994 | Ledley |
| 5,310,348 | A * | 5/1994 | Miller ........................ 434/262 |
| 5,313,229 | A | 5/1994 | Gilligan et al. |
| 5,313,230 | A | 5/1994 | Venolia et al. |
| 5,317,336 | A | 5/1994 | Hall |
| 5,329,289 | A | 7/1994 | Sakamoto et al. |
| 5,341,459 | A | 8/1994 | Backes |
| 5,351,692 | A | 10/1994 | Dow et al. |
| 5,358,408 | A * | 10/1994 | Medina ........................ 434/262 |
| 5,359,193 | A | 10/1994 | Nyui et al. |
| 5,368,487 | A * | 11/1994 | Medina ........................ 434/262 |
| 5,374,942 | A | 12/1994 | Gilligan et al. |
| 5,379,663 | A | 1/1995 | Hara |
| 5,384,460 | A | 1/1995 | Tseng |
| 5,390,128 | A | 2/1995 | Ryan et al. |
| 5,390,296 | A | 2/1995 | Crandall et al. |
| 5,396,267 | A | 3/1995 | Bouton |
| 5,397,323 | A | 3/1995 | Taylor et al. |
| 5,398,044 | A | 3/1995 | Hill |
| 5,402,499 | A | 3/1995 | Robison et al. |
| 5,402,582 | A | 4/1995 | Raab |
| 5,402,680 | A | 4/1995 | Korenaga |
| 5,403,191 | A * | 4/1995 | Tuason ........................ 434/262 |
| 5,417,696 | A | 5/1995 | Kashuba et al. |
| 5,428,748 | A | 6/1995 | Davidson et al. |
| 5,436,542 | A | 7/1995 | Petelin et al. |
| 5,436,640 | A | 7/1995 | Reeves |
| 5,452,615 | A | 9/1995 | Hilton |
| 5,457,479 | A | 10/1995 | Cheng |
| 5,457,793 | A | 10/1995 | Elko et al. |
| 5,467,763 | A | 11/1995 | McMahon et al. |
| 5,473,344 | A | 12/1995 | Bacon et al. |
| 5,474,082 | A | 12/1995 | Junker |
| 5,481,914 | A | 1/1996 | Ward |
| 5,491,477 | A | 2/1996 | Clark et al. |
| 5,512,919 | A | 4/1996 | Araki |
| 5,514,150 | A | 5/1996 | Rostoker |
| 5,524,195 | A | 6/1996 | Clanton, III et al. |
| 5,526,022 | A | 6/1996 | Donahue et al. |
| 5,530,455 | A | 6/1996 | Gillick et al. |
| 5,543,821 | A | 8/1996 | Marchis et al. |
| 5,546,508 | A * | 8/1996 | Jain ................... B25J 9/1635 700/260 |
| 5,547,383 | A | 8/1996 | Yamaguchi |
| 5,550,562 | A | 8/1996 | Aoki et al. |
| 5,550,563 | A | 8/1996 | Matheny et al. |
| 5,570,111 | A | 10/1996 | Barrett et al. |
| 5,573,286 | A * | 11/1996 | Rogozinski ............ A61B 17/82 289/1.2 |
| 5,576,727 | A | 11/1996 | Rosenberg et al. |
| 5,583,407 | A | 12/1996 | Yamaguchi |
| 5,591,924 | A | 1/1997 | Hilton |
| 5,592,401 | A | 1/1997 | Kramer |
| 5,604,345 | A | 2/1997 | Matsuura |
| 5,611,731 | A | 3/1997 | Bouton et al. |
| 5,623,582 | A | 4/1997 | Rosenberg |
| 5,623,642 | A | 4/1997 | Katz et al. |
| 5,624,398 | A * | 4/1997 | Smith ................... A61B 34/70 604/95.01 |
| 5,627,531 | A | 5/1997 | Posso et al. |
| 5,628,686 | A | 5/1997 | Svancarek et al. |
| 5,635,897 | A | 6/1997 | Kuo |
| 5,638,421 | A | 6/1997 | Serrano et al. |
| 5,652,603 | A | 7/1997 | Abrams |

(56) References Cited

U.S. PATENT DOCUMENTS

| | | |
|---|---|---|
| 5,666,138 A | 9/1997 | Culver |
| 5,680,141 A | 10/1997 | Didomenico et al. |
| 5,691,747 A | 11/1997 | Amano |
| 5,694,153 A | 12/1997 | Aoyagi et al. |
| 5,722,071 A | 2/1998 | Berg et al. |
| 5,722,836 A * | 3/1998 | Younker ................. 434/272 |
| 5,724,106 A | 3/1998 | Autry et al. |
| 5,724,264 A | 3/1998 | Rosenberg et al. |
| 5,734,108 A | 3/1998 | Walker et al. |
| 5,740,083 A | 4/1998 | Anderson et al. |
| 5,745,057 A | 4/1998 | Sasaki et al. |
| 5,746,752 A * | 5/1998 | Burkhart ............ A61B 17/0469 606/139 |
| 5,749,577 A | 5/1998 | Couch et al. |
| 5,755,620 A | 5/1998 | Yamamoto et al. |
| 5,763,874 A | 6/1998 | Luciano et al. |
| 5,767,836 A | 6/1998 | Scheffer et al. |
| 5,771,037 A | 6/1998 | Jackson |
| 5,795,228 A | 8/1998 | Trumbull et al. |
| 5,808,568 A | 9/1998 | Wu |
| 5,808,603 A | 9/1998 | Chen |
| 5,818,426 A | 10/1998 | Tierney et al. |
| 5,825,305 A | 10/1998 | Biferno |
| 5,828,295 A | 10/1998 | Mittel et al. |
| 5,831,593 A | 11/1998 | Rutledge |
| 5,841,133 A | 11/1998 | Omi |
| 5,841,423 A | 11/1998 | Carroll, Jr. et al. |
| 5,841,428 A | 11/1998 | Jaeger et al. |
| 5,844,673 A | 12/1998 | Ivers |
| 5,873,732 A * | 2/1999 | Hasson ................. 434/262 |
| 5,876,325 A * | 3/1999 | Mizuno et al. ............ 600/102 |
| 5,877,748 A | 3/1999 | Redlich |
| 5,879,327 A | 3/1999 | Moreau DeFarges et al. |
| 5,889,506 A | 3/1999 | Lopresti et al. |
| 5,912,661 A | 6/1999 | Siddiqui |
| 5,917,486 A | 6/1999 | Rylander |
| 5,919,159 A | 7/1999 | Lilley et al. |
| 5,936,613 A | 8/1999 | Jaeger et al. |
| 5,947,743 A * | 9/1999 | Hasson ................. 434/262 |
| 5,954,689 A | 9/1999 | Poulsen |
| 5,963,196 A | 10/1999 | Nishiumi et al. |
| 5,986,638 A | 11/1999 | Cheng |
| 6,007,550 A * | 12/1999 | Wang et al. .............. 606/139 |
| 6,017,273 A | 1/2000 | Pelkey |
| 6,031,222 A | 2/2000 | Carapelli |
| 6,063,095 A * | 5/2000 | Wang et al. .............. 606/139 |
| 6,078,311 A | 6/2000 | Pelkey |
| 6,078,876 A | 6/2000 | Rosenberg et al. |
| 6,097,499 A | 8/2000 | Casey et al. |
| 6,097,964 A | 8/2000 | Nuovo et al. |
| 6,104,379 A | 8/2000 | Petrich et al. |
| 6,143,006 A * | 11/2000 | Chan ............ A61B 17/0469 289/1.2 |
| 6,183,364 B1 | 2/2001 | Trovato |
| 6,192,432 B1 | 2/2001 | Slivka et al. |
| 6,241,574 B1 | 6/2001 | Helbing |
| 6,259,433 B1 | 7/2001 | Meyers |
| 6,280,327 B1 | 8/2001 | Leifer et al. |
| 6,293,798 B1 | 9/2001 | Boyle et al. |
| 6,295,608 B1 | 9/2001 | Parkes et al. |
| 6,300,038 B1 | 10/2001 | Shimazu et al. |
| 6,349,301 B1 | 2/2002 | Mitchell et al. |
| 6,398,557 B1 * | 6/2002 | Hoballah ................. 434/272 |
| 6,418,329 B1 | 7/2002 | Furuya |
| 6,546,390 B1 | 4/2003 | Pollack et al. |
| 6,633,224 B1 | 10/2003 | Hishida et al. |
| 6,692,485 B1 * | 2/2004 | Brock ................ A61B 34/77 414/5 |
| 6,760,751 B1 | 7/2004 | Hachiya et al. |
| 6,767,037 B2 * | 7/2004 | Wenstrom, Jr. .... A61B 17/0401 289/1.2 |
| 6,780,016 B1 * | 8/2004 | Toly ................. 434/262 |
| 6,810,281 B2 * | 10/2004 | Brock et al. ............ 600/427 |
| 6,887,082 B2 * | 5/2005 | Shun ................. 434/267 |
| 6,991,627 B2 * | 1/2006 | Madhani et al. ........ 606/1 |
| 7,594,815 B2 * | 9/2009 | Toly ................. 434/262 |
| 8,328,860 B2 * | 12/2012 | Strauss ........... A61B 17/12022 623/1.11 |
| 8,814,905 B2 * | 8/2014 | Sengun ........... A61B 17/0401 289/1.5 |
| 8,821,543 B2 * | 9/2014 | Hernandez ........ A61B 17/0401 606/139 |
| 8,834,170 B2 * | 9/2014 | Kurenov .......... A61B 17/0469 434/262 |
| 8,882,660 B2 * | 11/2014 | Phee ............... A61B 1/00147 600/139 |
| 8,926,661 B2 * | 1/2015 | Sikora ............. A61B 17/0401 606/232 |
| 9,345,468 B2 * | 5/2016 | Sengun ........... A61B 17/0401 |
| 2001/0018354 A1 | 8/2001 | Pigni |
| 2001/0045978 A1 | 11/2001 | McConnell et al. |
| 2002/0072674 A1 | 6/2002 | Criton et al. |
| 2002/0087166 A1 * | 7/2002 | Brock ................ A61B 34/20 606/130 |
| 2003/0043206 A1 | 3/2003 | Duarte |
| 2003/0112269 A1 | 6/2003 | Lentz et al. |
| 2004/0033476 A1 * | 2/2004 | Shun ................. 434/262 |
| 2004/0076444 A1 | 4/2004 | Badovinac et al. |
| 2004/0142314 A1 * | 7/2004 | Hasson et al. ............ 434/262 |
| 2004/0193393 A1 | 9/2004 | Keane |
| 2005/0064378 A1 * | 3/2005 | Toly ................. 434/262 |
| 2005/0187747 A1 | 8/2005 | Paxson et al. |
| 2005/0251206 A1 | 11/2005 | Maahs |
| 2006/0178556 A1 * | 8/2006 | Hasser ............... A61B 1/05 600/102 |
| 2006/0252019 A1 * | 11/2006 | Burkitt et al. ............. 434/262 |
| 2007/0093858 A1 | 4/2007 | Gambale |
| 2007/0156172 A1 | 7/2007 | Alvarado |
| 2007/0166682 A1 * | 7/2007 | Yarin et al. ............. 434/267 |
| 2007/0172803 A1 * | 7/2007 | Hannaford et al. ........ 434/262 |
| 2007/0238081 A1 * | 10/2007 | Koh ................. 434/262 |
| 2007/0287992 A1 * | 12/2007 | Diolaiti ................ G05B 19/19 606/1 |
| 2008/0064017 A1 * | 3/2008 | Grundmeyer et al. ..... 434/262 |
| 2008/0065105 A1 * | 3/2008 | Larkin ............. A61B 1/00087 606/130 |
| 2008/0071291 A1 * | 3/2008 | Duval ............. A61B 1/00087 606/130 |
| 2008/0218770 A1 * | 9/2008 | Moll ................ A61G 7/0503 356/614 |
| 2010/0291520 A1 * | 11/2010 | Kurenov et al. ............. 434/262 |

FOREIGN PATENT DOCUMENTS

| | | |
|---|---|---|
| EP | 0 358 989 B1 | 7/1994 |
| EP | 0 875 819 B1 | 10/2002 |
| GB | 2 237 160 A | 4/1991 |
| GB | 2 347 199 A | 8/2000 |
| WO | WO 96/16397 | 5/1996 |
| WO | WO 96/24398 | 8/1996 |
| WO | WO 96/32679 | 10/1996 |
| WO | WO 00/77689 A1 | 12/2000 |
| WO | WO 01/00630 A1 | 1/2001 |
| WO | WO 01/67297 A1 | 9/2001 |
| WO | WO 03/000319 A1 | 1/2003 |

OTHER PUBLICATIONS

Adelstein, B. et al., Design and Implementation of a Force Reflecting Manipulandum for Manual Control Research, DSC-vol. 42, Advances in Robotics, ASME 1992, pp. 1-12.

Akamatsu et al., Multimodal Mouse: A Mouse-Type Device with Tactile and Force Display, Presence, vol. 3, No. 1 pp. 73-80, 1994.

ATIP98.059: Virtual Reality (VR) Development at SERI (Korea), Asian Technology Information Program (ATIP) Jul. 20, 1998, pp. 1-9.

Aukstakalnis, S. et al., the Art and Science of Virtual Reality Silicon Mirage, 1992, Peachpit Press, Inc., Berkeley, CA, pp. 129-180.

Baigrie, S. et al., Electric Control Loading-A Low Cost, High Performance Alternative, Proceedings, Nov. 6-8, 1990, pp. 247-254.

(56) References Cited

OTHER PUBLICATIONS

Bejczy, A., Sensors, Controls, and Man-Machine Interface for Advanced Teleoperation, Science, vol. 208, No. 4450, 1980, pp. 1327-1335.

Bejczy, A. et al., Kinesthetic Coupling Between Operator and Remote Manipulator, International Computer Technology Conference, The American Society of Mechanical Engineers, San Francisco, CA, Aug. 12-15, 1980, pp. 1-9.

Bejczy, A. et al., A Laboratory Breadboard System for Dual-Arm Teleoperation, SOAR '89 Workshop, JSC, Houston, Jul. 25-27, 1989.

Bejczy, A. et al., Universal Computer Control System (UCCS) for Space Telerobots, Jet Propulsion Laboratory, California Institute of Technology, Pasadena, CA, pp. 317-324.

Bjork, S. et al., An Alternative to Scroll Bars on Small Screens, Play: Applied Research on Art and Technology, Viktoria Institute, Box 620, SE-405 30 Gothenburg, Sweden, pp. 1-2.

Bouguila, L. et al., Effect of Coupling Haptics and Stereopsis on Depth Perception in Virtual Environment, Precision and Intelligence Laboratory, Tokyo Institute of Technology, 4259 Nagatsuta cho Midori ku Yokohama shi 226-8503-Japan.

Brooks, T. et al., Hand Controllers for Teleoperation: A State-of-the-Art Technology Survey and Evaluation, 1985, NASA Jet Propulsion Laboratory, California Institute of Technology, Pasadena, CA.

Burdea, G. et al., Distributed Virtual Force Feedback, IEEE Workshop on "Force Display in Virtual Environments and its Application to Robotic Teleoperation," May 2, 1993, Atlanta, GA.

Calder, B. et al., Design of a Force-Feedback Touch-Inducing Actuator for Teleoperator Robot Control, Submitted to the Department of Mechanical Engineering and Electrical Engineering in partial Fulfillment of the requirements of the degree of Bachelors of Science in Mechanical Engineering and Bachelor of Science in Electrical Engineering at the Massachusetts Institute of Technology, May 1983.

Caldwell, D. et al., Enhanced Tactile Feedback (Tele-Taction) using a Multi-Functional Sensory System, Dept. of Electronic Eng., University of Salford, Salford, M5 4WT, UK, 1993.

Cyberman Technical Specification, Logitech Cyberman SWIFT Supplement, Revision 1.0, Apr. 5, 1994, pp. 1-29.

Eberhardt, S. et al., OMAR-A Haptic Display for Speech Perception by Deaf and Deaf-Blind Individuals, IEEE Virtual Reality Annual International Symposium, Sep. 18-22, 1993, Seattle Washington.

Eberhardt, S. et al., Inducing Dynamic Haptic Perception by the Hand: System Description and Some Results, Dynamic Systems and Control, 1994, vol. 1, presented at 1994 International Mechanical Engineering Congress and Exposition, Chicago Illinois, Nov. 6-11, 1994.

Fukumoto, M. et al., Active Click: Tactile Feedback for Touch Panels, NTT DoCoMo Multimedia Labs, Japan.

Gobel, M. et al., Tactile Feedback Applied to Computer Mice, International Journal of Human-Computer Interaction, vol. 7, No. 1, pp. 1-24, 1995.

Gotow, J. et al., Controlled Impedance Test Apparatus for Studying Human Interpretation of Kinesthetic Feedback, The Robotics Institute and Deptartmetn of Mechanical Engineering, Carnegie Mellon University, Pittsburgh, PA 15213, pp. 332-337.

Hansen, W., Enhancing Docuemtns with Embedded Programs: How Ness extends Insets in the Andrew Toolkit, 1990, Information Technology Center, Carnegie Mellon University, Pittsburgh, PA 15213.

Hasser, C. et al., Tactile Feedback with Adaptive Controller for a Force-Reflecting Haptic Display Part 1: Design, 1996, Armstrong Laboratory, Human Systems Center, Air Force Materiel Command, Wright-Patterson AFB OH 45433.

Hasser, C. et al., Tactile Feedback for a Force-Reflecting Haptic Display, Thesis Submitted to the School of Engineering of the University of Daytona, Dayton OH, Dec. 1995.

Hasser, C., Force-Reflecting Anthropomorphic Hand Masters, Crew Systems Directorate Biodynamics and Biocommunications Division, Wright-Patterson AFB OH 45433-7901, Jul. 1995, Interim Report for the Period Jun. 1991-Jul. 1995.

Hinckley, K. et al., Haptic Issues for Virtual Manipulation, A Dissertation presented to the Faculty of the School of Engineering and Applied Science at the University of Virginia, in Partial Fulfillment of the Requirement for the Degree Doctor of Philosophy (Computer Science), Dec. 1996.

Howe, R., A Force-Reflecting Teleoperated Hand System for the Study of Tactile Sensing in Precision Manipulation, Proceedings of the 1992 IEEE Conference in Robotics and Automation, Nice, France-May 1992.

Iwata, H., Pen-Based Haptic Virtual Environment, Institute of Engineering Mechanics, University of Tsukuba, Japan, 1993.

Jacobsen, S. et al., High Performance, Dextrous Telerobotic Manipulator with Force Reflection, Intervention/ROV '91, Conference & Exposition, May 21-23, 1991, Hollywood, FL.

Johnson, A., Shape-Memory Alloy Tactical Feedback Actuator, Phase I-Final Report, Air Force SABIR Contract F33-88-C-0541, Armstrong Aerospace Medical Research Laboratory, Human Systems Division, Air Force Systems Command, Wright-Patterson Air Force Base, OH 45433.

Jones, L. et al., A Perceptual Analysis of Stiffness, Experimental Brain Research, 1990, vol. 79, pp. 150-156.

Kaczmarek, K. et al., Tactile Displays, Virtual Environment Technologies, pp. 349-414.

Kelley, A. et al., MagicMouse: Tactile and Kinesthetic Feedback in the Human-Computer Interface using an Electromagnetically Actuated Input/Output Device, Department of Electrical Engineering, University of British Columbia, Canada, Oct. 19, 1993.

Lake, S.L., Cyberman from Logitech, web site at http://www.ibiblio.org/GameBytes/issue21/greviews/cyberman/html, as available via the Internet and printed May 29, 2002.

MacLean, K., Designing with Haptic Feedback, Interval Research Corporation, 1801 Page Mill Road, Palo Alto, CA 94304, 2000.

Mine, M., Isaac: A Virtual Environment Tool for the Interactive Construction of Virtual Worlds, Department of Computer Science, University of North Carolina Chapel Hill, 1995.

Picinbono, G. et al., Extrapolation: A Solution for Force Feedback, Virtual Reality and Prototyping, Jun. 1999, Laval, France.

Wloka, M., Interacting with Virtual Reality, Science and Technology Center for Computer Graphics and Scientific Visualization, Brown University Site, Department of Computer Science, 1995.

eRENA, Pushing Mixed Reality Boundaries, Deliverable 7b.1, Final, Version 1.0.

Real Time Graphics, The Newsletter of Virtual Environment Technologies and Markets, Aug. 1998, vol. 7, No. 2.

1998 IEEE International Conference on Robotics and Automation, May 16-20, 1998, Lueven, Belgium.

Patent Cooperation Treaty, International Search Report, International Application No. PCTUS0802019, mailed Jul. 14, 2008.

* cited by examiner

SYSTEMS AND METHODS FOR REAL-TIME WINDING ANALYSIS FOR KNOT DETECTION

FIELD OF THE INVENTION

The present invention relates generally to knot detection. The present invention relates more specifically to systems and methods for real-time winding analysis for knot detection.

BACKGROUND

To close a wound, or during a surgery, a doctor or nurse may need to tie a knot to complete a suture. Typically, a standard array of knots is used to close a suture, and a doctor or nurse would learn some or all of these knots in school or training. Part of the training process may include supervision by a trained doctor or nurse who may watch the trainee tie the knot, and may examine the completed knot to ensure that the correct knot type was used, and that the knot was tied correctly. When the knot is tied using string, and the trainer is available to watch the trainee tie the knot, it is relatively straightforward for the trainer to recognize the knot used. However, knot detection by a computer is significantly more difficult.

Knot detection, in general, is an NP-complete problem, which means that it takes an exponential amount of time, computationally, to recognize a knot based on the knot presented. The use of general-purpose knot-detection algorithms in a simulation tool may impair the speed and effectiveness of the simulation tool as a training device, as they require a significant amount of time to execute. Existing knot detection algorithms also impose constraints on the definition of knots input into the algorithm that may render those algorithms less desirable for use in a simulation system.

SUMMARY

Embodiments of the present invention comprise systems, methods, and computer-readable media for real-time winding analysis for knot detection. For example, one embodiment of the present invention is a method comprising receiving a first wrapping signal indicating a first wrapping of the simulated thread around a second tool to create a first loop. The method further comprises determining a first wrapping direction based at least in part on the first wrapping signal; receiving a first tightening signal indicating a pulling of a first end of the simulated thread through the first loop; determining a first half-hitch based at least in part on the first winding direction and the first tightening signal; and outputting the first half-hitch. In another embodiment, a computer-readable media comprises code for a carrying out such a method.

These illustrative embodiments are mentioned not to limit or define the invention, but to provide examples to aid understanding thereof. Illustrative embodiments are discussed in the Detailed Description, and further description of the invention is provided there. Advantages offered by various embodiments of this invention may be further understood by examining this specification.

BRIEF DESCRIPTION OF THE DRAWINGS

These and other features, aspects, and advantages of the present invention are better understood when the following Detailed Description is read with reference to the accompanying drawings, wherein.

DETAILED DESCRIPTION

Embodiments of the present invention provide systems, methods, and computer-readable media for real-time winding analysis for knot detection.

Illustrative Real-Time Winding Analysis for Knot Detection

Figure 1:
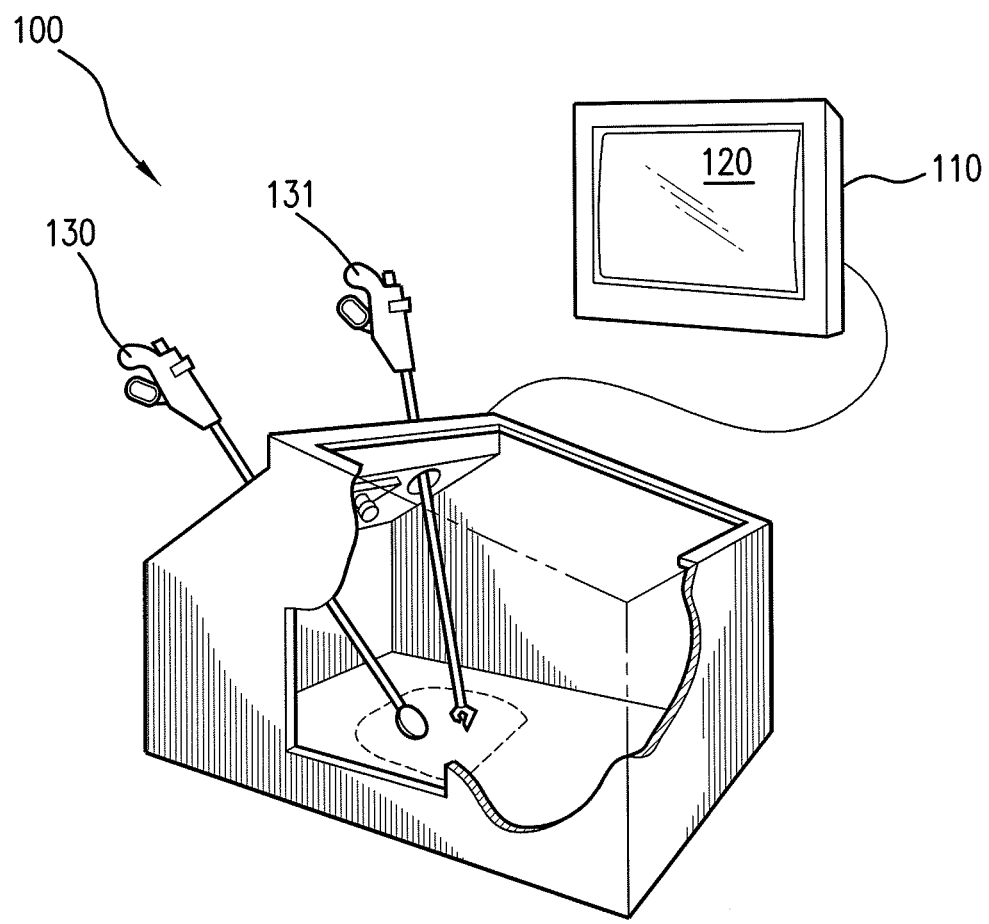
FIG. 1 shows an illustrative system for real-time winding analysis for knot detection according to one embodiment of the present invention.

FIG. 1 shows an illustrative system for real-time winding analysis for knot detection according to one embodiment of the present invention. According to the illustrative embodiment shown in FIG. 1, a system for real-time winding analysis comprises a laparoscopy simulation system 100. The laparoscopy simulation system 100 comprises a computer 110, an integrated display 120, and two laparoscopy simulation tools 130, 131. The computer 110 executes a laparoscopic surgery simulation application (not shown). The laparoscopy simulation tools 130, 131 are in communication with the computer 110 and are used by a user to interact with the simulation application. The simulation tools 130, 131 comprise sensors which are capable of detecting manipulation of the tools, and transmitting sensor data to the computer 110. The simulation tools 130, 131 also comprise actuators capable of outputting haptic effects to the simulation tools 130, 131.

During a simulated surgery, the simulation application may display a view of the simulated surgery on the display 120 for the user to view. The user manipulates the simulation tools 130, 131 to provide signals to the simulation application, which interprets the signals as movements of the simulated tools. The simulation application may then update the display 120 based on the user's manipulation of the simulation tools 130, 131.

During a surgery, a doctor may need to suture an incision. A doctor typically sutures an incision by using a thread to stitch the incision closed, and then tying the thread off, which will hold the two flaps of skin or organic material together to allow them to rejoin and heal. In a laparoscopic surgery, the process of suturing a wound is typically more difficult than during a more invasive surgery, or when suturing a wound or incision on the patient's skin. Laparoscopic surgery is performed by inserting special laparoscopic tools into a patient via one or more small incisions. The surgery is performed by a surgeon who watches video images on a screen transmitted by a camera inserted into one of the incisions, and manipulates the tools to perform the surgery based on the video images. During a laparoscopic surgery, internal incisions within the patient may be made, which are sutured at the end of the surgery to allow the patient to heal properly. Training for a laparoscopic surgery, including suturing a wound using laparoscopic instruments, typically requires significant training, often with simulation systems.

To train for making sutures in a laparoscopic surgery, a doctor or medical student may use a laparoscopy simulation system. In such an event, the user uses the simulation tools 130, 131 to suture the incision with a simulated thread, and then ties a simulated knot. To tie the knot, the user grasps one end of the simulated thread (the first end) with one of the simulation tools (the first tool) 130, and winds the other end of the thread (the second end) around the other simulation tool (the second tool) 131. It should be noted that the first end and second end need not be the actual terminal parts of the thread, and are not used in such a limited fashion herein. Rather, the ends simply refer to two different locations on the thread that are sufficiently far apart to allow a knot to be tied—for some sutures, the two "ends" need not be very far apart at all. In a surgery simulation, the first end may refer to the portion of the thread extending from one side of the incision, while the second end may refer to the portion of the thread extending from the other side of the incision.

The computer 110 detects the winding of the thread around the second tool 131, and determines the direction of the winding. Once the winding is completed, the user grasps the first end of the thread with the second tool 131, and pulls the first end of the simulated thread through the winding, and pulls the winding tight. The computer 110 detects the movement of the first end of the simulated thread through the winding, and the tightening of the winding as a half-hitch. The user then ties additional, successive half-hitches having the same or different winding directions. The computer 110 tracks each of the half-hitches and the direction of the winding in each of the half-hitches.

Once the user releases the thread with the first tool 130, the computer 110 determines that the user has completed the knot. The computer 110 then determines the type of knot the user has tied by analyzing the sequence of half-hitches and winding directions. For example, in this illustrative embodiment, if the user has tied a knot with two half-hitches, each of which having the same winding direction, the computer 110 detects the knot as a "granny" (or slip) knot. Or, if the user has tied a knot with two half-hitches, each with a different winding direction, the computer 110 detects the knot as a square knot. By detecting the half-hitches and windings in real-time as the user is tying the knot, the illustrative system 100 is able to correctly identify the type of knot, and to provide real-time feedback to the user, such as whether the user is correctly tying the desired knot.

According to this illustrative embodiment, the system 100 may also output haptic effects to the first and/or second tools 130, 131 to provide feedback to the user. For example, the computer 110 may detect the tightening of a winding and output a resistive force on one or both tools 130, 131 to indicate that the half-hitch is being tightened. The computer may also output haptic effects to the second tool 131 while the user is wrapping the thread around the tool to emulate forces the user might experience during a real surgery, such as contact between the tool 131 and a part of the patient's body, or movement of the tool resulting from force on the thread. Still further haptic effects could be output to provide a more realistic simulation environment.

Systems and Methods for Real-Time Winding Analysis for Knot Detection

Figure 2:
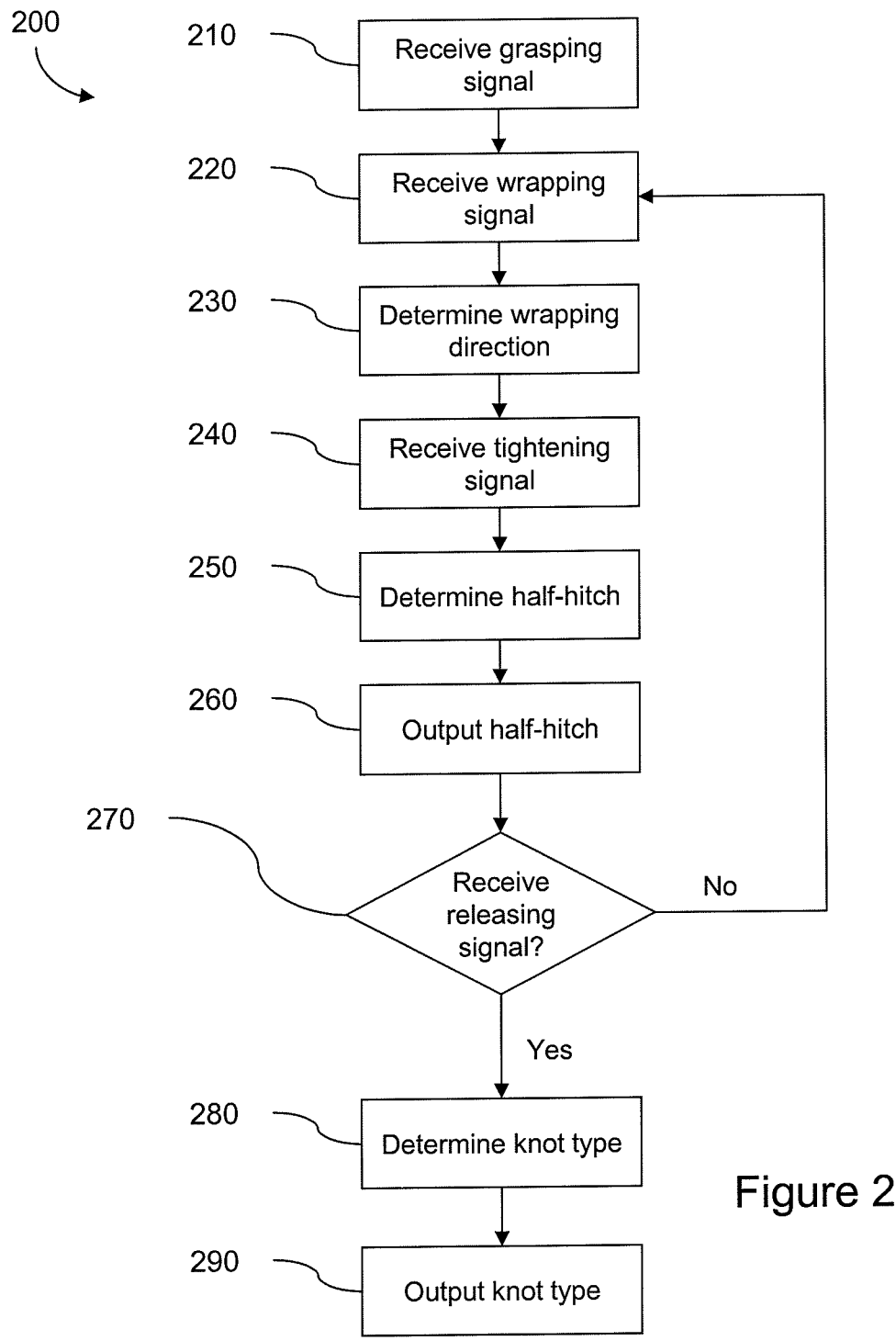
FIG. 2 is a flowchart showing a method for real-time winding analysis for knot detection according to one embodiment of the present invention.

FIG. 2 is a flowchart showing a method 200 for real-time winding analysis for knot detection according to one embodiment of the present invention. The method 200 shown in FIG. 2 will be discussed in terms of the components shown in the system 100 in FIG. 1.

In block 210, the computer 110 receives a grasping signal. The grasping signal indicates that the first tool 130 has grasped one end of a simulated thread (referred to as the first end). For example, according to one embodiment of the present invention, a user may view an image of a thread shown in the display 120 that has been used to suture an incision. The user may also view images of the position and orientation of the simulation tools 130, 131 on the display 100. The user may manipulate the first tool 130 to be in proximity to the simulated thread, which sends signals to the computer 110 to indicate that the user has moved the first tool 130. The user may then manipulate the first tool 130 to grasp one end of the thread. When the user grasps the thread with the first tool 130, the computer receives a signal indicating a grasping of the simulated thread with the first tool 130.

In one embodiment of the present invention, when the user grasps the first end of the simulated thread with the first tool 130, the computer also determines a relative position of the first end of the simulated thread relative to the second end of the simulated thread, and a position and orientation of the first tool 130 with respect to the second tool 131. In some embodiments of the present invention, the relative positions of the first end of the thread and the second end of the thread may be used to determine when a wrapping of the simulated thread is occurring, or a direction of the wrapping (described below). However, determining the relative positions may not be necessary. Accordingly, some embodiments may not determine the relative positions of the first end of the simulated thread and the second end of the simulated thread. Further, some embodiments may not determine a relative position and orientation of the first tool 130 with respect to the second tool 131.

In block 220, the computer 110 receives a wrapping signal. The wrapping signal indicates that the user is wrapping, or has wrapped, the other end of the simulated thread (referred to as the second end) around the second simulation tool 131. To wrap the thread around the second tool 131, the user may manipulate the second tool to interact with the simulated thread. By viewing the movement of the second tool 131 on the display, and the second tool's interaction with the thread, the user may be able to wrap the thread around the tool to create a loop. While the user is manipulating the second tool 131 to wrap the simulated thread, the computer 110 receives a first wrapping signal indicating a first wrapping of the simulated thread around the second tool to create a first loop. Alternatively, in one embodiment, the computer 110 may receive a first wrapping signal after the user has completed a loop.

According to one embodiment of the present invention, a wrapping signal may comprise data indicative of a contact between a thread and a simulation tool. For example, the wrapping signal may comprise a vector indicating the normal force between a simulated thread and the second tool 131 at a location. In another embodiment, the wrapping signal may comprise a plurality of vectors indicating normal forces between a simulated thread and the second tool 131 at a plurality of locations. In some embodiments, the wrapping signal may be sent in real-time, i.e. as the user wraps a simulated thread around a simulation tool. Additionally, a plurality of wrapping signals may be received by the computer 110 as the user wraps the thread around the tool. In some embodiments, the wrapping signal may be sent at an interval, or after a minimum length of thread has been wrapped, or after a wrapping is complete.

Figure 3:
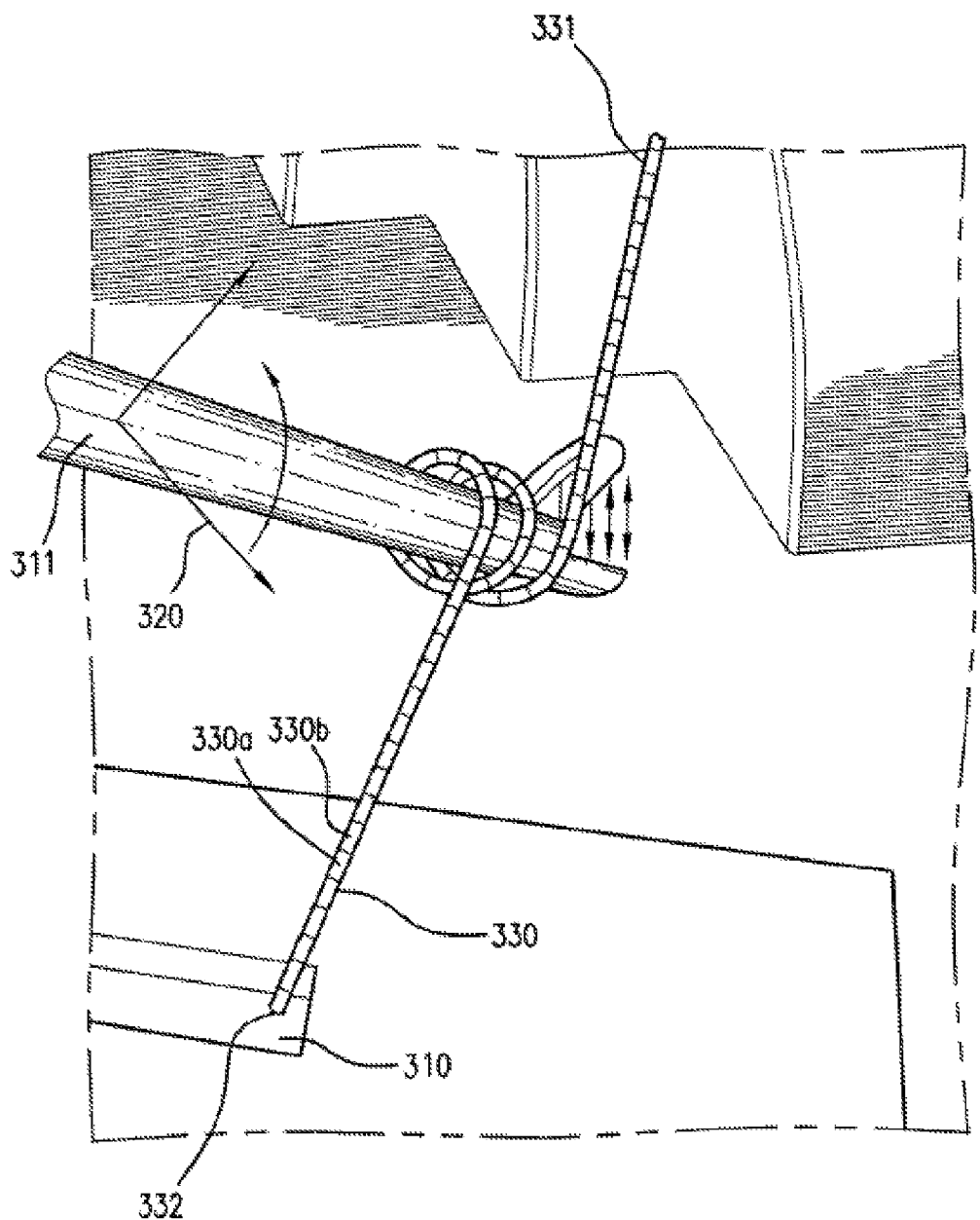
FIG. 3 is an illustration of a simulated thread wrapped around a laparoscopic tool according to one embodiment of the present invention.

In block 230, the computer determines the wrapping direction. According to one embodiment of the present invention, as the user wraps the simulated thread around the second tool 311, the computer 110 determines the direction of the wrapping or winding. For example, the computer may define a set of axes 320 based on the position and orientation of the second tool 311, as may be seen in FIG. 3. FIG. 3 is an illustration of a simulated thread 330 wrapped around a laparoscopic tool 311. In this embodiment of the present invention, the axes 320 are fixed with respect to the second tool 311, and move and rotate as the second tool 311 moves and rotates. Since the thread wraps around the tools, the thread will also tend to move about the axes. However, in some embodiments, the thread may wrap around the tool without contacting the tool. In such embodiments, a thread in proximity to the tool, such was within a threshold distance, may be detected as a winding.

As the simulated thread 330 is wrapped around the second tool 311, the computer may calculate normal forces exerted by the second tool 311 on the simulated thread 330 at one or more points along the length of the thread 330. The normal forces may be represented as vectors by the computer 101, and the vectors may be defined having directions relative to the axes 320. After the computer 101 has calculated normal vectors along the length of the thread, the computer 101 may then determine the direction of the winding. For example, the computer 101 may analyze the normal vectors in sequence beginning at the first end 331 of the thread 330, and continuing to the second end 332 of the thread 330. As the computer 101 analyzes the normal vectors, the normal vectors will tend to change direction in a clockwise or counter-clockwise direction with respect to the axes, as the thread 330 wraps around the second tool 311, which may be seen in FIG. 4.

In one embodiment of the present invention, the computer 110 may determine a direction of a wrapping in real-time. For example, as the computer 110 receives wrapping signals, the computer 110 may compute changes in direction of normal forces between the thread and the second tool 311. The computer 110 may use the changes in direction to determine a direction of the wrapping as the user wraps the thread around the second tool 311.

Figure 4:
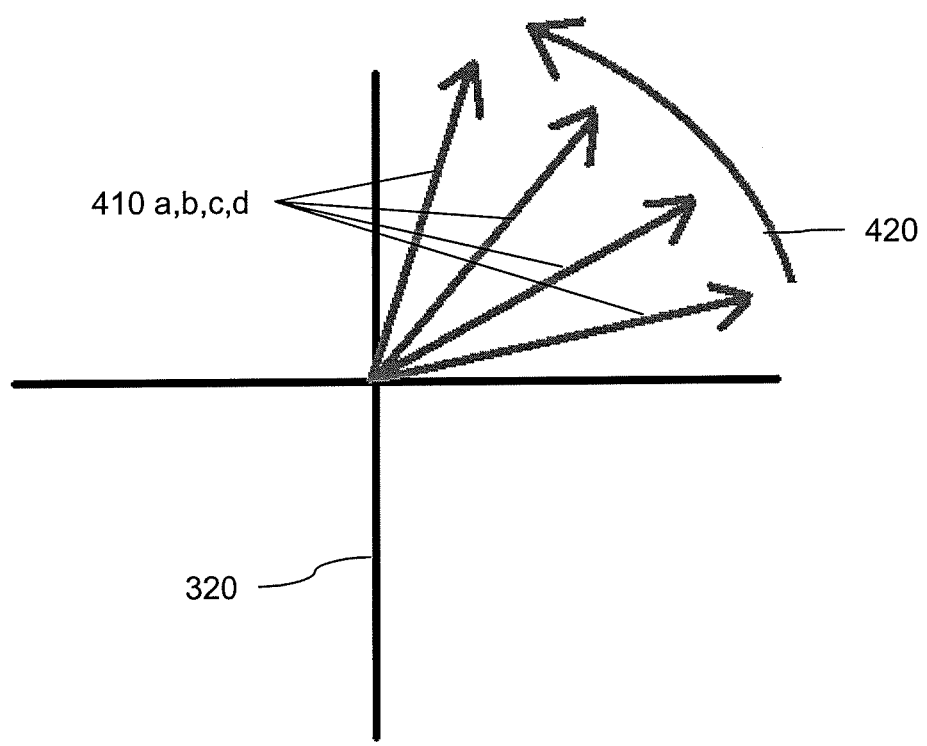
FIG. 4 is a diagram of normal forces rotating about a center point on a pair of axes according to one embodiment of the present invention.

FIG. 4 is a diagram of normal forces rotating about a center point on a pair of axes. The axes 320 in FIG. 4 are the axes 320 shown in FIG. 3. The normal vectors 410a-d represent normal vectors for a portion of the simulated thread 330 as it wraps around the second tool 311. Normal vector 410a, the right-most vector, represents the normal vector at a point on the simulated thread 330 nearer to the first end 310, which is grasped by the first tool 310, than normal vectors 410b-d. As the simulated thread 330 wraps around the second tool 311, the computer calculates the normal vectors 410a-d in succession. The curved arrow 420 indicates the direction of winding around the second tool 311. Thus, by analyzing the changes in direction of each successive normal vector 410a-d, the computer may determine the direction of winding of the thread 330 around the second tool 311.

In some embodiments of the present invention, a computer may determine the direction of a first wrapping based at least in part on how the thread was initially grasped. For example, a user may grasp a first end of a thread such that, in order to pull the first end through a loop, the tools must cross (referred to as a scissor's move). In such a case, the direction of the wrapping is opposite to the apparent direction. This results from the crossing maneuver, which effectively reverses the direction of the wrapping. Thus, in one embodiment of the present invention, a computer may determine that a scissor's move has occurred, and will determine the direction of the wrapping based at least in part on the scissor's move.

In one embodiment of the present invention, the thread 330 is represented as a series of discrete pieces, such as pieces 330a and 330b. Each of these pieces has a single normal vector associated with it. By breaking the thread into pieces and only calculating one normal per piece, the number of calculations needed may be significantly reduced. In other embodiments, each pieces may have a plurality of normal vectors associated with its contact with the second tool 311.

In one embodiment of the present invention, a thread is represented by a series of discrete pieces referred to as nodes. To determine a winding direction, the computer makes calculations based on the thread's nodes. The computer 101 can calculate a wrap angle based on the angles formed by the thread nodes as they wind about the tool axis In such an embodiment, the computer 101 may compute the wrap angle, θ, according to the following equation:

$$\theta = \int \Delta\theta = \sum_{i \in C} \theta_i - \theta_{i-1} \qquad (1)$$

for nodes i in contact set C, where each $\theta_i$ is the four quadrant arctangent evaluation of $\theta_i = \tan^{-1}(n \cdot x / n \cdot z)$. n is the vector from the closest point on the second tool 311 to node i, and x, z are the axes 320 perpendicular to the longitudinal axis of the second tool 311. By definition, an overhand wrap angle has a positive sign, and an underhand wrap angle has a negative sign. Thus, the computer 101 may determine the direction of a wrapping based on the sign of the angle resulting from equation (1).

In block 240, the computer 101 receives a tightening signal indicating a pulling of the first end 311 of the simulated thread through the first loop. Once a user has created a loop or winding, the user may close a knot or half-hitch by pulling the first end of the thread through the loop. According to one embodiment of the present invention, a user may close a half-hitch by manipulating the second tool 311 to pull the first end of the thread through the loop made by wrapping the thread around the second tool 311.

In block 250, the computer determines that the user has completed a half-hitch. After pulling the first end 311 of the thread 330 through the first loop, the user may pull the half-hitch tight, which may cause the computer 110 to receive a signal indicating that the half-hitch has been completed. Alternatively, the computer 110 may determine that the half-hitch has been completed based on the user's manipulation of the tools, such as by a motion made to tighten the half-hitch.

In block 260, the computer outputs a signal indicating that a half-hitch has been made. According to one embodiment of the present invention, the system may generate a haptic effect when the user pulls the half-hitch tight. For example, the system shown in FIG. 1 may output a force to resist motion of one or both tools 310, 311 to indicate to a user that the half-hitch has been pulled tight. In addition, the system may output a visual and/or audible indication that the half-hitch has been completed. For example, the system may briefly change the color of the thread to green when a half-hitch has been successfully completed. The change in color may be accompanied by a bell or beep sound, or the audible indication may accompany a different or additional visual indication.

The system may also output the half-hitch by storing an information describing the half-hitch to a computer-readable medium. For example, in one embodiment of the present invention, a system for winding analysis for knot detection may execute a simulation to test a user's ability to tie one or more knots. In such an embodiment, when the user completes a half-hitch, the system may store information relating to the half-hitch to a computer-readable medium, such as a hard disk, to be used when grading the user's performance. Information relating to the half-hitch may include the direction of the winding, a number of windings, an indication of a quality of the half-hitch, a number of attempts needed to complete the half-hitch, or a time to complete the half-hitch.

In block 270, the computer may receive a releasing signal indicating that the user has released both ends of the thread. Such a signal may indicate that the knot has been completed. If a releasing signal is received, it is an indication that the user has completed the knot, and the method progresses to step 280. However, the user may not have completed the knot at this point, and so the user may elect to begin another winding. In such a case the system may receive a wrapping signal. If no releasing signal is received, and a wrapping signal is received, the method returns to step 220. In such a case, the user is mostly likely attempting to tie another half-hitch.

In block 280, the computer 101 determines the type of knot the user has tied. In one embodiment of the present invention, the computer 101 may determine that the user has tied a "granny" or slip knot if the knot includes two half-hitches, both of which having the same winding direction. In one embodiment, the computer 101 may determine that the user has tied a square knot if the knot includes two half-hitches, each of which having different winding directions. In one embodiment, the computer 101 may determine that the user has tied a surgeon's knot if the knot includes a half-hitch having a plurality of windings. Other embodiments can detect knots based on a sequence of half-hitches.

In block 290, the computer 101 outputs the knot type. In one embodiment, the computer 101 may generate output similar to the outputs generated for completing a half-hitch. For example, the system may output a visual and/or audible indication that the knot has been completed. For example, the system may briefly change the color of the thread to green when the knot has been successfully completed, or to red if the knot was incorrectly tied. The change in color may be accompanied by a bell or beep sound, or the audible indication may accompany a visual indication.

The computer may also output the knot by storing an information describing the knot to a computer-readable medium. For example, in one embodiment of the present invention, a system for winding analysis for knot detection may execute a simulation to test a user's ability to tie one or more knots. In such an embodiment, when the user completes a knot, the system may store information relating to the knot to a computer-readable medium, such as a hard disk, to be used when grading the user's performance. Information relating to the knot may include the type of knot attempted, the type of knot completed, the number of attempts to tie the knot, the time needed to tie the knot, the number and type of half-hitches used to make the knot, or a quality of the knot.

Figure 5:
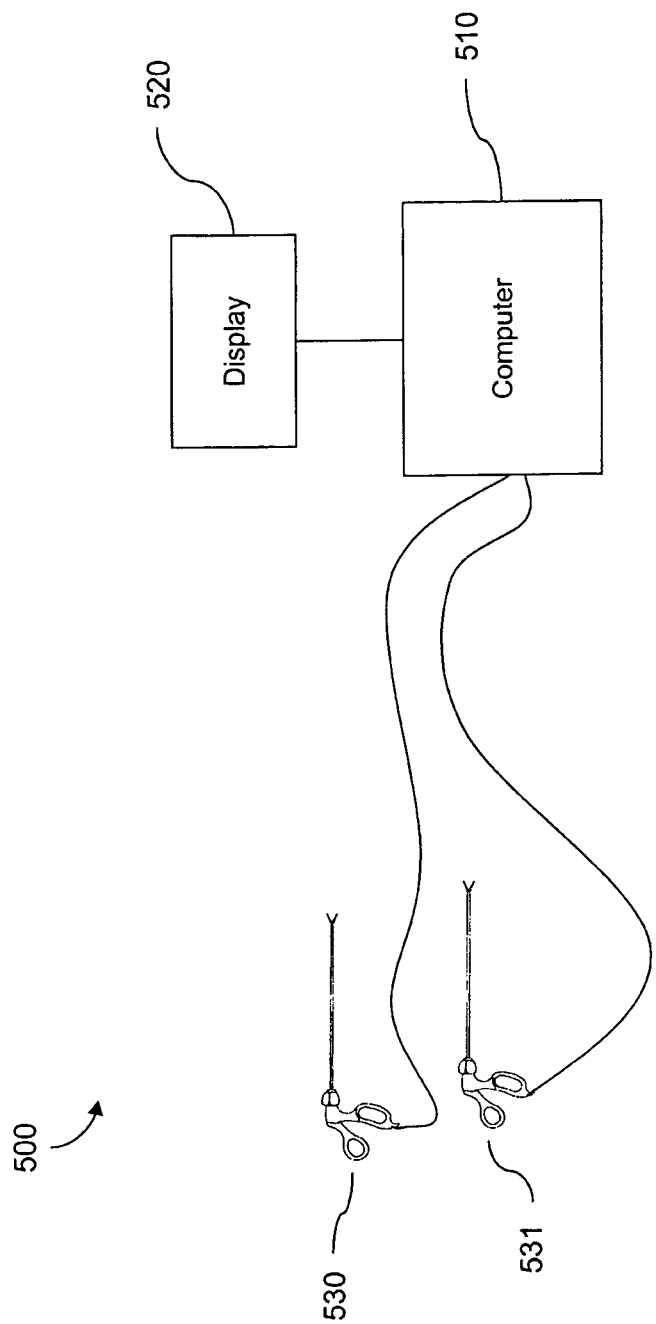
FIG. 5 is an illustration of a system for winding analysis for knot detection according to one embodiment of the present invention.

Referring now to FIG. 5 which is an illustration of a system 500 for winding analysis for knot detection according to one embodiment of the present invention. The system 500 comprises a computer 510, a display 520, and two laparoscopy tools 530, 531. The computer 510 comprises a processor (not shown) in communication with the display 520 and the laparoscopy tools 530, 531. The processor is configured to receive a grasping signal, receive a first wrapping signal, and determine a first winding direction based at least in part on the first wrapping signal. The processor is also configured to receive a first tightening signal, determine a first half-hitch based at least in part on the first winding direction and the first tightening signal, and to output the first half-hitch. In one embodiment of the present invention, the processor is configured to execute the methods described above with respect to FIGS. 2-4.

In the embodiment shown in FIG. 5, the simulation tools 530, 531 comprise laparoscopic simulation tools. The tools 530, 531 are coupled to a device which generally confines the movement of the tools to a limited number of degrees of freedom. For example, in the embodiment shown in FIG. 1, the tools are rotatably coupled to housing. The tools range of motion in the embodiment of FIG. 1 is limited to three degrees of rotational freedom, and one degree of freedom in translation. In the embodiment shown in FIG. 1, the tools are coupled to the housing at a pivot point. The tools can pivot in two degrees of freedom at the pivot point, which may be a ball and socket type joint, a linkage mechanism, or other joint that allows two degrees of rotational freedom. The tools are also capable of twisting about their longitudinal axis in a third degree of rotational freedom. Lastly, the tools can be moved linearly along their longitudinal axis, to allow the ends of the tools within the housing to be moved into or out of the housing. Other embodiments of the present invention may allow for greater or fewer degrees of freedom. For example, in one embodiment of the present invention, the tools 530, 531 are configured to rotate about two axes—an x-axis and a y-axis—to provide a full range of rotary motion to a user. In still a further embodiment, the simulation tools 530, 531 may be moveable in six degrees of freedom—three rotary and three translatory.

In addition, in some embodiments of the present invention, the simulation tools may not be bounded by a coupling to a housing. For example, according to one embodiment of the present invention, the user may wear special gloves with sensors, where the gloves are capable of transmitting their position and orientation to a computer. In another embodiment, the system may comprise video cameras or other remote sensors that are able to capture a user's movements in space without requiring the user to wear special gloves or other equipment.

Some embodiments of the present invention may provide haptic feedback to a user. For example, in one embodiment of the present invention, the laparoscopy tools 530, 531 comprise actuators configured to output haptic effects. In one such embodiment, each of the haptic tools 530, 531 comprise actuators in communication with the computer 510. Examples of suitable actuators may be found in co-pending U.S. patent application Ser. No. 10/196,717 entitled "Pivotable Computer Interface" filed Jul. 15, 2002, the entirety of which is incorporated herein by reference. Other actuators may be suitable as well. In such an embodiment, the haptic tools 530, 531 are configured to receive one or more actuator signals from the computer 510, the actuator signals configured to cause the actuators to output a haptic effect. In some embodiments, only one of the simulation tools 530, 531 may comprise an actuator. In some embodiments, the simulations tools 530, 531 may comprise a plurality of actuators.

Haptically-enabled embodiments of the present invention may be capable of outputting a variety of haptic effects. For example, one embodiment of the present invention is configured to output haptic effects intended to replicate forces encountered during a laparoscopic surgery, such as resistance to movement of the tools within incisions, effects indicating contact with parts of a patient's body, vibrations or movements associated with a patient's movement (e.g. heartbeats, breathing, etc.), or other forces encountered during a simulated surgery.

Some embodiments may output other haptic effects intended to signal the user to a status or message. For example, one embodiment of the present invention may provide a haptic effect to a simulation tool 530, 531 to indicate that the user is incorrectly tying a knot. Suitable effects may be vibrations or resistance to movement of the tools.

Referring again to FIGS. 1 and 5, embodiments of the present invention can be implemented in digital electronic circuitry, or in computer hardware, firmware, software, or in combinations of them. In one embodiment, a computer may comprise a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage or transmission device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include, such as a router, private or public network, or other transmission device. The processor, and the processing, described may be in one or more structures, and may be dispersed through one or more structures. The processor may comprise code for carrying out one or more of the methods (or parts of methods) described herein.

Figure 6:
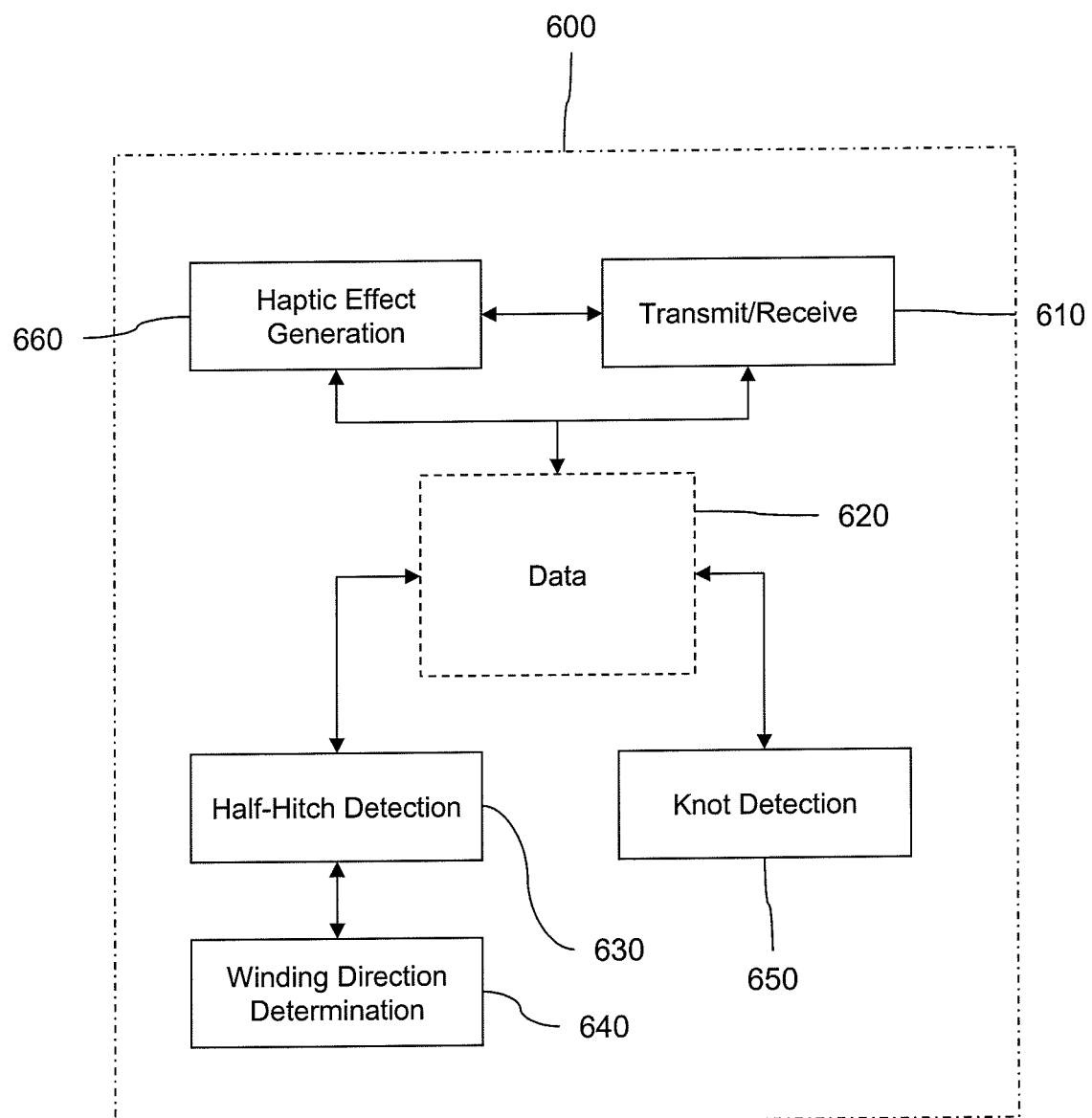
FIG. 6 is a block diagram of a software application for winding analysis for knot detection according to one embodiment of the present invention.

For example, program code for a software application to perform methods according to one embodiment of the present invention may comprise a series of interconnected software modules. For example, FIG. 6 is a block diagram of a software application for winding analysis for knot detection according to one embodiment of the present invention. The software application will be described in relation to the system shown in FIG. 1. The software application 600 comprises a transmit/receive block 610, a half-hitch detection block 630, a knot detection block 650, and a winding direction determination block 640. The application also includes a memory allocation 620 for data that can be accessed by any of the blocks 610, 630, 640, 650 of the software application 600.

In the embodiment shown in FIG. 6, the transmit/receive block 610 is configured to receive signals from and transmit signals to the first and second tools 130, 131. For example, transmit/receive block 610 is configured to receive a grasping signal, a wrapping signal, a tightening signal, and a releasing signal. The transmit/receive block is configured to store data associated with the signals it receives into data block 620 for use by other components of the application. Transmit/receive block 610 is also configured to output signals to the first and second tools 130, 131, such as an actuator signal to cause an actuator to output a haptic effect to the first and/or second tools 130, 131. In the embodiment shown, the transmit/receive block can receive information for generating haptic effects from the haptic effect generation block 660.

Half-hitch detection block 630 is configured to read data from the data block 620 and to determine if a half-hitch has been made. Half-hitch detection block 630 employs winding direction determination block 640 to determine the direction of a winding, and then is able to determine when a half-hitch is made based on data read from the data block 620. Such data may comprise data parameters or information received from signals received by the transmit/receive block. For example, the half-hitch detection block 630 may perform half-hitch detection as described in relation to FIG. 2. Winding direction determine block 640 determines the winding direction of a thread as described relative to other embodiments of the present invention.

Knot detection block 650 is configured to determine when a knot has been completed, and to determine a knot type based on data read from data block 620. Such data may comprise data parameters or information received by the transmit/receive block 610. Knot determination employs the method of knot detection described with respect to FIG. 2, but other embodiments may comprise other methods of knot determination.

Haptic effect generation block 660 is configured to generate haptic effects to be output to the first and/or second tools 130, 131. The information for generating the haptic effects may be gained from the data block 620, or from information received from the transmit/receive block 610. The haptic effect generation block 660 transmits haptic effect information to the transmit/receive block 610, which then transmits an actuator signal based at least in part on the haptic effect information to the first and/or second tools 130, 131.

While the embodiment described with respect to FIG. 6 describes one embodiment of the present invention with a particular architecture and particular functional divisions, other architectures and functionality are possible and are intended to be within the scope of the present invention. For example, in one embodiment of the present invention, the software application comprises a single process. In another embodiment, the software application comprises a plurality of process in communication with each other. Still further embodiments, such as client-server embodiments are possible.

General

The foregoing description of the embodiments of the invention has been presented only for the purpose of illustration and description and is not intended to be exhaustive or to limit the invention to the precise forms disclosed.

Numerous modifications and adaptations thereof will be apparent to those skilled in the art without departing from the spirit and scope of the invention.

That which is claimed is:

1. A method, comprising:
   receiving, by a processor, a first wrapping signal from a sensor in communication with a tool, the tool comprising an actuator, the first wrapping signal indicating a first wrapping of a simulated thread around the tool to create a first loop;
   determining, by a processor, a wrap angle based at least in part on a plurality of normal vectors along a portion of the simulated thread, the plurality of normal vectors based at least in part on the wrapping signal;
   determining, by a processor, a first winding direction based at least in part on the wrap angle;
   receiving, by a processor, a first tightening signal indicating a pulling of a first end of the simulated thread through the first loop;
   determining, by a processor, a first half-hitch based at least in part on the first winding direction and the first tightening signal; and
   outputting, by a processor, the first half-hitch and an actuator signal configured to cause the actuator to output a haptic effect.

2. The method of claim 1, further comprising:
   receiving a second wrapping signal indicating a second wrapping of the simulated thread around the tool to create a second loop;
   determining a second wrap angle based at least in part on a second plurality of normal vectors along a portion of the simulated thread, the second plurality of normal vectors based at least in part on the second wrapping signal;
   determining a second winding direction based at least in part on the second wrap angle;
   receiving a second tightening signal indicating a pulling of the first end of the simulated thread through the second loop;
   determining a second half-hitch based at least in part on the second winding direction and the second tightening signal;
   determining a knot type based at least in part on the first half-hitch and the second half-hitch; and
   outputting the knot type.

3. The method of claim 2, further comprising:
   receiving a third wrapping signal indicating a third wrapping of the simulated thread around the tool to create a third loop;
   determining a third wrap angle based at least in part on a third plurality of normal vectors along a portion of the simulated thread, the third plurality of normal vectors based at least in part on the third wrapping signal;
   determining a third winding direction based at least in part on the third wrap angle;
   receiving a third tightening signal indicating a pulling of the first end of the simulated thread through the third loop;
   determining a third half-hitch based at least in part on the third winding direction and the third tightening signal; and
   wherein determining a knot type is further based at least in part on the third half-hitch.

4. The method of claim 1, wherein the tool comprises a second tool, and further comprising receiving a releasing signal indicating a releasing of the simulated thread by a first tool.

5. The method of claim 2, wherein the knot type comprises one of a granny knot, a square knot, or a surgeon's knot.

6. The method of claim 1, wherein the tool comprises a second tool, and further comprising transmitting an actuator signal to cause an actuator to output a haptic effect to a first tool or the second tool.

7. The method of claim 1, wherein the tool comprises a second tool, and further comprising receiving a grasping signal indicating a grasping of a simulated thread with a first tool.

8. A non-transitory computer-readable medium comprising program code configured to cause a processor to:
   receive a first wrapping signal from a sensor in communication with a tool, the tool comprising an actuator, the first wrapping signal configured to indicate a first wrapping of a simulated thread around the tool to create a first loop;
   determine, by a processor, a wrap angle based at least in part on a plurality of normal vectors along a portion of the simulated thread, the plurality of normal vectors based at least in part on the wrapping signal
   determine, by a processor, a first winding direction based at least in part on the wrap angle;
   receive a first tightening signal indicating a pulling of a first end of the simulated thread through the first loop;
   determine a first half-hitch based at least in part on the first winding direction and the first tightening signal; and
   output the first half-hitch and an actuator signal configured to cause the actuator to output a haptic effect.

9. The non-transitory computer-readable medium of claim 8, wherein the program code is further configured to cause the processor to:
   receive a second wrapping signal indicating a second wrapping of the simulated thread around the tool to create a second loop;
   determine a second wrap angle based at least in part on a second plurality of normal vectors along a portion of the simulated thread, the second plurality of normal vectors based at least in part on the second wrapping signal;
   determine a second winding direction based at least in part on the second wrap angle;
   receive a second tightening signal indicating a pulling of the first end of the simulated thread through the second loop;
   determine a second half-hitch based at least in part on the second winding direction and the second tightening signal;
   determine a knot type based at least in part on the first half-hitch and the second half-hitch; and
   output the knot type.

10. The non-transitory computer-readable medium of claim 8, wherein the tool comprises a second tool, and the program code is further configured to cause the processor to transmit an actuator signal to cause an actuator to output a haptic effect to a first tool or the second tool.

11. The non-transitory computer-readable medium of claim 8, wherein the tool comprises a second tool, and the program code is further configured to cause the processor to receive a grasping signal indicating a grasping of a simulated thread with a first tool.

12. A system, comprising:
a first simulation tool comprising an actuator;
a second simulation tool;
a display; and
a processor in communication with the first simulation tool, the second simulation tool, and the display, the processor configured to:
  receive a first wrapping signal from a sensor in communication with the first simulation tool;
  determine a wrap angle based at least in part on a plurality of normal vectors along a portion of the simulated thread, the plurality of normal vectors based at least in part on the wrapping signal;
  determine a first winding direction based at least in part on the wrap angle;
  receive a first tightening signal;
  determine a first half-hitch based at least in part on the first winding direction and the first tightening signal; and
  output the first half-hitch and an actuator signal configured to cause the actuator to output a haptic effect.

13. The system of claim 12, wherein the processor is further configured to:
  receive a second wrapping signal;
  determine a second wrap angle based at least in part on a second plurality of normal vectors along a portion of the simulated thread, the second plurality of normal vectors based at least in part on the second wrapping signal;
  determine a second winding direction based at least in part on the second wrap angle;
  receive a second tightening signal;
  determine a second half-hitch based at least in part on the second winding direction and the second tightening signal;
  determine a knot type based at least in part on the first half-hitch and the second half-hitch; and
  output the knot type.

14. The system of claim 12, wherein
the first simulation tool comprises a first actuator,
the second simulation tool comprises a second actuator, and
the processor is further configured to:
  output a first actuator signal to the first actuator to cause the first actuator to output a haptic effect to the first simulation tool, and
  output a second actuator signal to the second actuator to cause the second actuator to output a haptic effect to the second simulation tool.

15. The system of claim 12, wherein the processor is further configured to receive a grasping signal.

16. The method of claim 1, wherein the simulated thread is represented by a plurality of nodes, and determining the wrap angle comprises computing $$\theta = \int \Delta\theta = \sum_{i \in C} \theta_i - \theta_{i-1},$$

for nodes i in contact set C, where each $\theta_i$ is the four quadrant arctangent evaluation of $\theta_i = \tan^{-1}(n \cdot x / n \cdot z)$, where n is the vector from the closest point on the second tool to node i, and x, z comprise the axes perpendicular to the longitudinal axis of the second tool.

17. The non-transitory computer-readable medium of claim 8, wherein the simulated thread is represented by a plurality of nodes, and wherein the program code is further configured to cause the processor to compute $$\theta = \int \Delta\theta = \sum_{i \in C} \theta_i - \theta_{i-1},$$

for nodes i in contact set C, where each $\theta_i$ is the four quadrant arctangent evaluation of $\theta_i = \tan^{-1}(n \cdot x / n \cdot z)$. z), where n is the vector from the closest point on the second tool to node i, and x, z comprise the axes perpendicular to the longitudinal axis of the second tool to determine the wrap angle.

18. The system of claim 12, wherein the simulated thread is represented by a plurality of nodes, and wherein the processor is further configured to compute $$\theta = \int \Delta\theta = \sum_{i \in C} \theta_i - \theta_{i-1},$$

for nodes i in contact set C, where each $\theta_i$ is the four quadrant arctangent evaluation of $\theta_i = \tan^{-1}(n \cdot x / n \cdot z)$, where n is the vector from the closest point on the second tool to node i, and x, z comprise the axes perpendicular to the longitudinal axis of the second tool to determine the wrap angle.

* * * * *